United States Patent [19]
Yomtov

[11] Patent Number: 4,630,615
[45] Date of Patent: Dec. 23, 1986

[54] APPARATUS FOR MEASURING IMPEDANCE

[75] Inventor: Barry M. Yomtov, Cooper City, Fla.

[73] Assignee: Cordis Corporation, Miami, Fla.

[21] Appl. No.: 612,553

[22] Filed: May 21, 1984

[51] Int. Cl.⁴ .............................................. H61B 5/00
[52] U.S. Cl. .................... 128/734; 128/419 C
[58] Field of Search ............... 128/734, 735, 419 P, 128/733, 741, 783, 784, 907, 419 C, 421–423; 324/62 R, 65 R, 57 PS

[56] References Cited

U.S. PATENT DOCUMENTS

| | | | |
|---|---|---|---|
| 3,645,267 | 2/1972 | Hagfors | 128/419 C |
| 3,769,986 | 11/1973 | Hermann | 128/419 |
| 3,784,908 | 1/1974 | Anderson | 128/734 |
| 3,876,933 | 4/1975 | Harrington | 324/62 R |
| 3,918,459 | 11/1975 | Horn | 128/419 |
| 3,989,051 | 11/1976 | Nozhnikov et al. | 128/421 |
| 4,068,669 | 1/1978 | Niemi | 128/419 |
| 4,088,141 | 5/1978 | Niemi | 128/421 |
| 4,102,347 | 7/1978 | Yukl | 128/421 |
| 4,167,189 | 9/1979 | Tachi et al. | 128/421 |
| 4,252,130 | 2/1981 | Le Pivert | 128/734 |
| 4,338,945 | 7/1982 | Kosugi et al. | 128/421 |
| 4,354,498 | 10/1982 | Weigert et al. | 128/419 |
| 4,390,023 | 6/1983 | Rise | 128/421 |
| 4,408,617 | 10/1983 | Auguste | 128/421 |

Primary Examiner—Edward M. Coven
Attorney, Agent, or Firm—Henry W. Collins; Thomas R. Vigil

[57] ABSTRACT

The apparatus comprises: a comparator for comparing the voltage at which the constant current pulses are being supplied to the load with an increasing reference voltage; a counter for counting the number of voltage pulses that are greater in magnitude than the increasing reference voltage over a sampling period; and signal processing circuitry for correlating the count of pulses over the sampling period with the impedance of the load required to generate that number of constant current pulses at the voltage required for same.

13 Claims, 7 Drawing Figures

FIG. 3A CURRENT OUTPUT PULSE (PIN 3)
FIG. 3B COMPARATOR OUTPUT (PIN 6)
FIG. 3C BUFFERED OUTPUT (PA 7)
PULSE TIMING WAVEFORMS
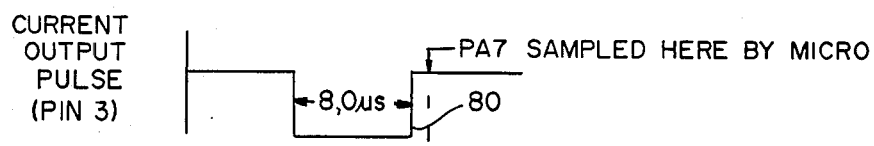
FIG. 4
TIMING DIAGRAM FOR TYPICAL LEAD IMPEDANCE OF 650 Ω
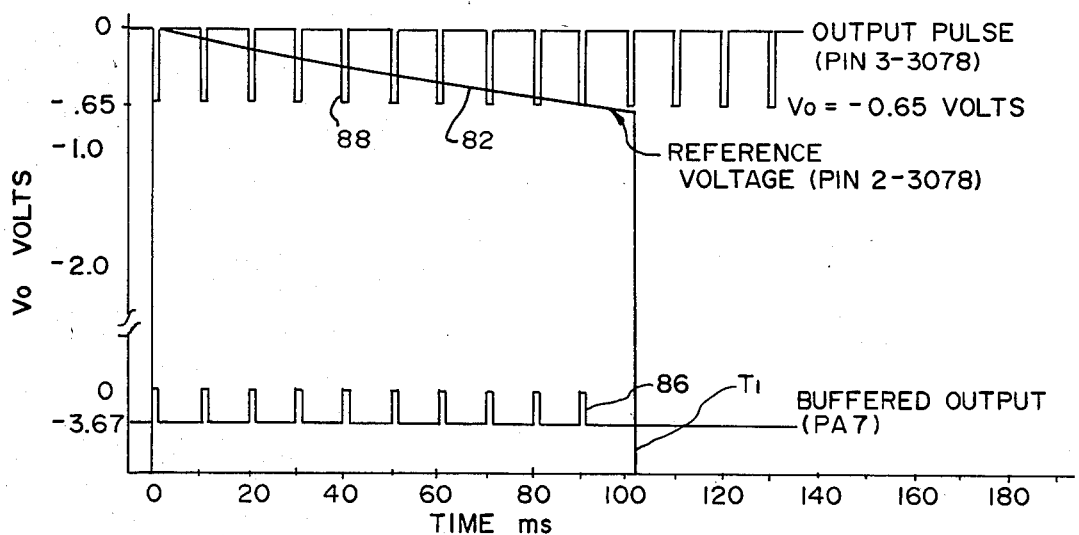
FIG. 5
TIMING DIAGRAM FOR HIGHER LEAD IMPEDANCE OF 1000 Ω
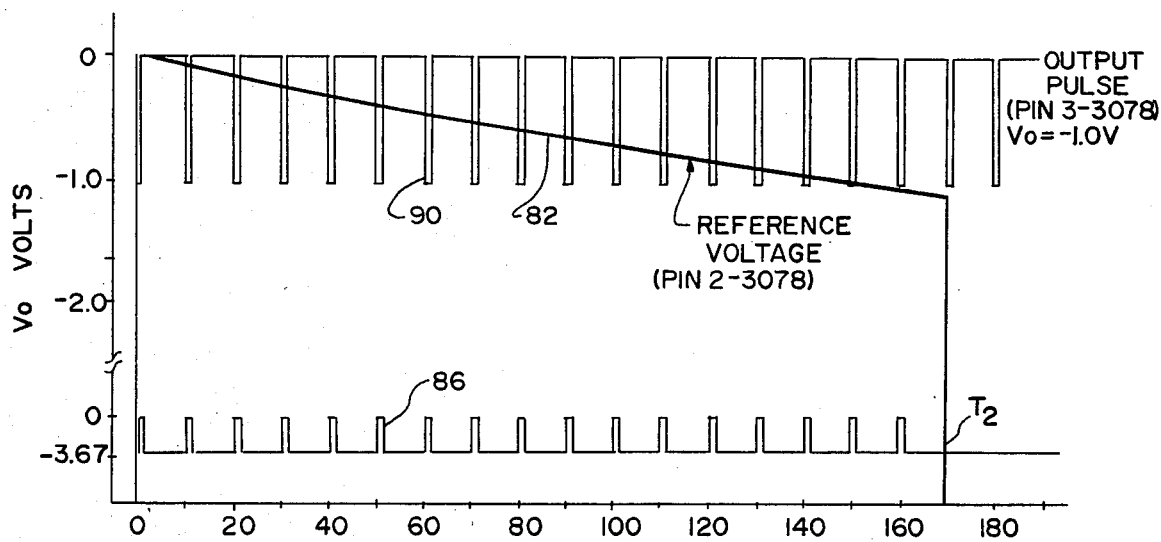

APPARATUS FOR MEASURING IMPEDANCE

BACKGROUND OF THE INVENTION

1. Field of the Invention

The present invention relates to a method and apparatus for measuring impedance. More specifically, the invention relates to an impedance measuring or determining apparatus which is incorporated in and used in a neural stimulating system where it is desirable to monitor and determine changes in a cathode lead impedance in a lead connected to a cathode implanted in the epidural space in a spine.

2. Description of the Prior Art

Heretofore, various apparatus for supplying neural stimulation pulses to nerves in the spine have been proposed. These prior neural stimulating devices and systems have also provided means for modifying, molding, patterning and altering the current signals supplied to the cathode electrode. Examples of these previously proposed neural stimulating systems and devices are disclosed in the following U.S. patents:

| U.S. Pat. No. | PATENTEE |
| --- | --- |
| 3,769,986 | Herrmann |
| 3,918,459 | Horn |
| 3,989,051 | Nozhnikov et al. |
| 4,068,669 | Niemi |
| 4,088,141 | Niemi |
| 4,102,347 | Yukl |
| 4,167,189 | Tachi et al. |
| 4,338,945 | Kosugi et al. |
| 4,354,498 | Weigert et al. |
| 4,390,023 | Rise |

An examination of these prior art patents will show that none of them disclose or suggest a lead impedance measuring system wherein pulses of a given amplitude are compared with a ramp voltage and wherein the given amplitude is related to the impedance then existing in a lead or circuit being monitored.

The Rise U.S. Pat. No. 4,390,023 merely discloses production of a patterned stimulus through multiple cathodes of a Transcutaneous Electrical Nerve Stimulator (T.E.N.S.).

The Weigert et al. U.S. Pat. No. 4,354,498 merely discloses a constant current method of measuring current across a known series resistance.

The Kosugi et al. U.S. Pat. No. 4,338,945 merely discloses randomizing of stimulus parameters and uses a microprocessor for this purpose.

The Nozhnikov et al. U.S. Pat. No. 3,980,951 merely discloses an external device similar to a T.E.N.S. having adjustable duration and amplitude.

The Herrmann U.S. Pat. No. 3,769,986 merely discloses a threshold analyzer using a current control device to determine-tissue thresholds using a controlled pulse current.

The Horn U.S. Pat. No. 3,918,459 merely discloses a constant current electrotherapy device which utilizes a DC signal and an alarm for high resistance and appears to be directed to an external device as opposed to an internally implanted device.

The Niemi U.S. Pat. No. 4,068,669 is directed to a stimulator fault protection circuit where the output current is monitored and the circuit limits high currents.

The Tachi et al. U.S. Pat. No. 4,167,189 is directed to an apparatus for transmission of information by electrocutaneous stimulus and measures $I_0$ and $V_0$ and then calculates $Z=V_0/I_0$. Here, the apparatus is directed to means for transmission of data and not to a technique for measuring.

The Niemi U.S. Pat. No. 4,088,141 discloses a fault circuit for a stimulator in a T.E.N.S. versus an implantable system. In this stimulator, a threshold impedance is monitored using a voltage divider in a time to voltage conversion within a microprocessor. This stimulator utilizes a voltage comparator and a constant current source. However, it does not compare voltage pulses required to maintain constant current pulses with a ramp voltage for the purpose of determining impedance as provided with the method and apparatus of the present invention.

Finally, the Yukl U.S. Pat. No. 4,102,347 discloses an electrical pain control system which monitors impedance threshold and limits a voltage applied if the impedance is too high. This system operates in a manner very similar to the stimulators disclosed in the Niemi patents referred to above.

As will be described in greater detail hereinafter, the method and apparatus of the present invention differ from the previously proposed methods and apparatus for neural stimulation which include some form of impedance monitoring circuitry by providing an impedance determining apparatus which includes a comparator for comparing an increasing ramp voltage with voltage pulses necessary to maintain constant current pulses supplied to the impedance.

SUMMARY OF THE INVENTION

According to the present invention there is provided in a neural stimulating apparatus of the type comprising a cathode adapted to be juxtaposed to the spinal cord in a body, an anode adapted to be placed in contact with the body, means for generating constant current output pulses which are supplied to the cathode, a cathode lead coupled between the pulse generating means and the cathode for carrying the pulses to the cathode and means for controlling (a) the generation of pulses and (b) the supplying of pulses to the cathode, the improvement comprising means coupled to the cathode lead for measuring the cathode impedance at the connection of said pulse generating means to the cathode lead, said means for determining changes in impedance comprising means for comparing the voltage pulses at which the constant current pulses are being supplied to the load with an increasing reference voltage, means for counting the number of voltage pulses that are greater in magnitude than the increasing reference voltage over a sampling period, and means for correlating said count of pulses over the sampling period with the impedance of the load presented by the lead and connections to tissue required to generate that number of constant current pulses at the voltage required for same.

BRIEF DESCRIPTION OF THE DRAWINGS

FIGS. 3A, 3B and 3C are three graphs of the waveforms of, respectively, the current output pulse supplied to the comparator shown in FIG. 2, the comparator output pulse, and the buffered output pulse supplied to the microprocessor port or line PA7.

FIG. 4 is a timing diagram of the operation of the apparatus shown in FIG. 2 for a typical cathode lead impedance of 650 ohms.

FIG. 5 is a timing diagram of the operation of the apparatus shown in FIG. 2 for a higher cathode lead impedance of 1,000 ohms.

DESCRIPTION OF THE PREFERRED EMBODIMENT

Figure 1:
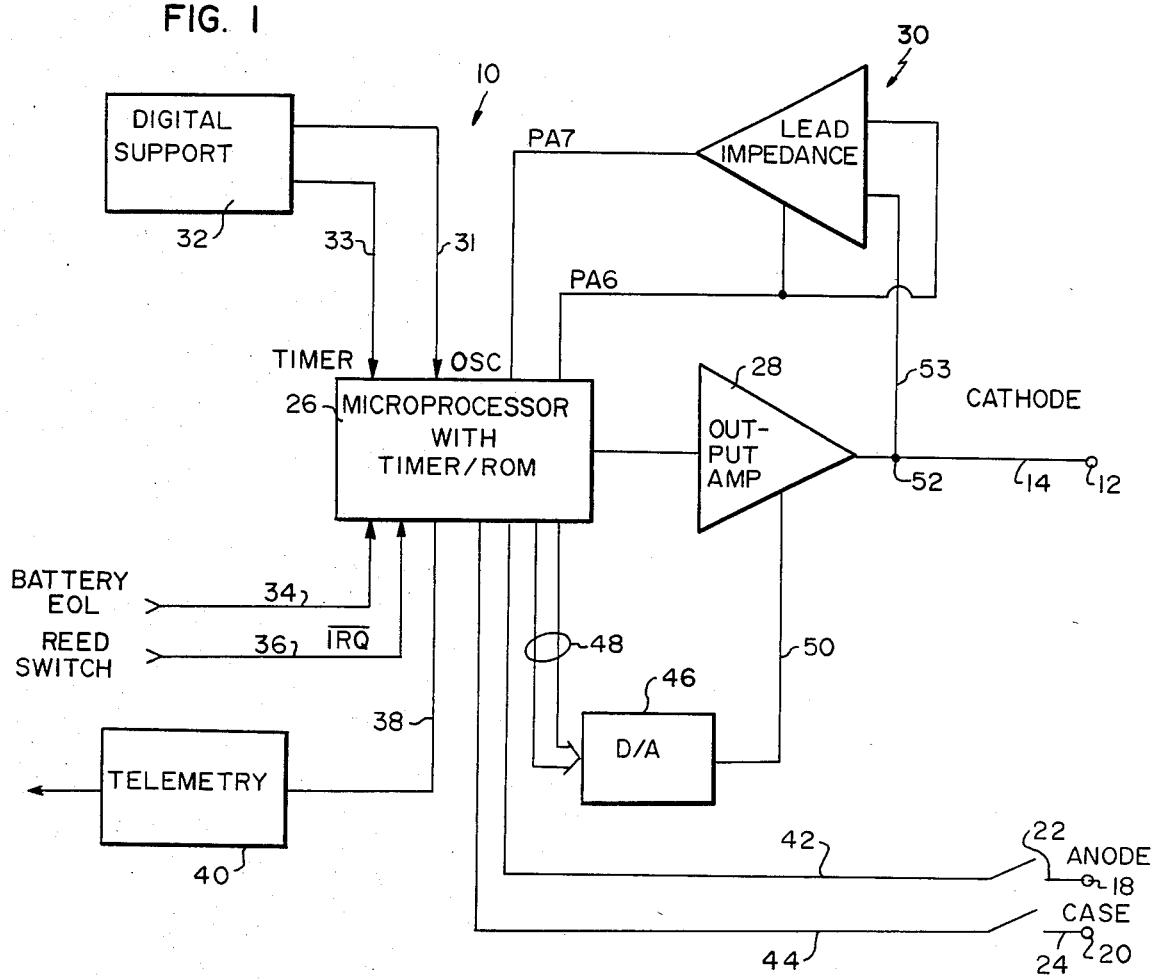
FIG. 1 is a block schematic circuit diagram of a neural stimulating system including the apparatus of the present invention for measuring the impedance of the load, namely, the circuit through a cathode lead and tissue at the cathode electrode.

Referring now to the drawings in greater detail, there is illustrated in FIG. 1, a block schematic circuit diagram of a neural stimulating system which is generally identified by reference numeral 10. The system 10 includes a cathode electrode shown schematically at 12 which is adapted to be inserted into the epidural space in a spinal cord so that electrical pulses can be supplied to the nerves in the spinal cord for blocking signals to the brain. Such a neural stimulating system 10 typically is utilized when it is desired to block pain signals to the brain but also could be used in the treatment of and/or for alleviating symptoms of, movement disorders spinal in nature, epilepsy, spasticity, cerebral palsy, etc. The cathode electrode 12 is mounted at the distal end of a cathode lead 14 which is coupled to a power amplifier which supplies current pulses to the cathode tip through the lead 14.

The electrical circuit from the cathode electrode 12 can be through an implanted anode electrode 18 or a case 20 of the implanted neural stimulating system 10. As shown, disconnect switches 22 and 24 are provided, respectively, between (a) the anode electrode 18 and a microprocessor 26 of the neural stimulating system 10 and (b) the case 20 and the microprocessor 26.

In the use of the neural stimulating system 10 having cathode electrode 12 inserted into the epidural space in the spine, it is important to monitor the impedance of the lead 14 that couples the electrode 12 to a power amplifier 28. In this respect, scar tissue might build up around the cathode electrode 12 thereby reducing its electrical connection to the body and its ability to supply current pulses to the body. Also, a monitoring of the lead 14 impedance will enable the system 10 to determine when there has been an open circuit resulting in high impedance or a short circuit.

In accordance with the teachings of the present invention, the neural stimulating system 10 is provided with an apparatus 30 for measuring, determining or monitoring impedance. This apparatus 30 will be described in greater detail below in connection with a description of the overall neural stimulating system 10.

As shown in FIG. 1, the neural stimulating system 10 includes the microprocessor 26 which receives an oscillating signal on an input line 31 from a digital support circuit 32 which also supplies a real time clock signal on an output line 33 to the microprocessor 26. Also, the microprocessor 26 includes a timer and a ROM.

A battery end-of-life indicating line 34 is coupled to another input of the microprocessor 26 as is a control input from a reed switch or a magnet switch on an input line 36.

It is to be understood that the neural stimulating system 10 can be implanted within a body and, by operation of the reed switch (not shown), the operation of the system 10 can be modified.

The microprocessor 26 further includes an output line 38 leading to a telemetry processing circuit 40 by which various data can be telemetered to an external source from the implanted neural stimulating system 10.

A ground for the system 10 is coupled by a line 42 or a line 44 to the anode electrode 18 or the case 20.

The power amplifier 28 is coupled to the microprocessor 26 for receiving electrical power therefrom and is controlled by the output from a digital-to-analog converter 46 which has digital input lines 48 connected thereto from the microprocessor 26 and an output line 50 for controlling operation of the power output amplifier 28. The output from the power amplifier 28 is supplied through the lead 14 to the cathode electrode 12.

In accordance with the teachings of the present invention, this output at a junction 52 is also supplied to an input line 53 to the impedance determining apparatus 30. The impedance determining apparatus 30 also has a voltage supplied thereto via a line PA6 from the microprocessor 26 and has an output line PA7 leading from the apparatus 30 to an input of the microprocessor 26.

Figure 2:
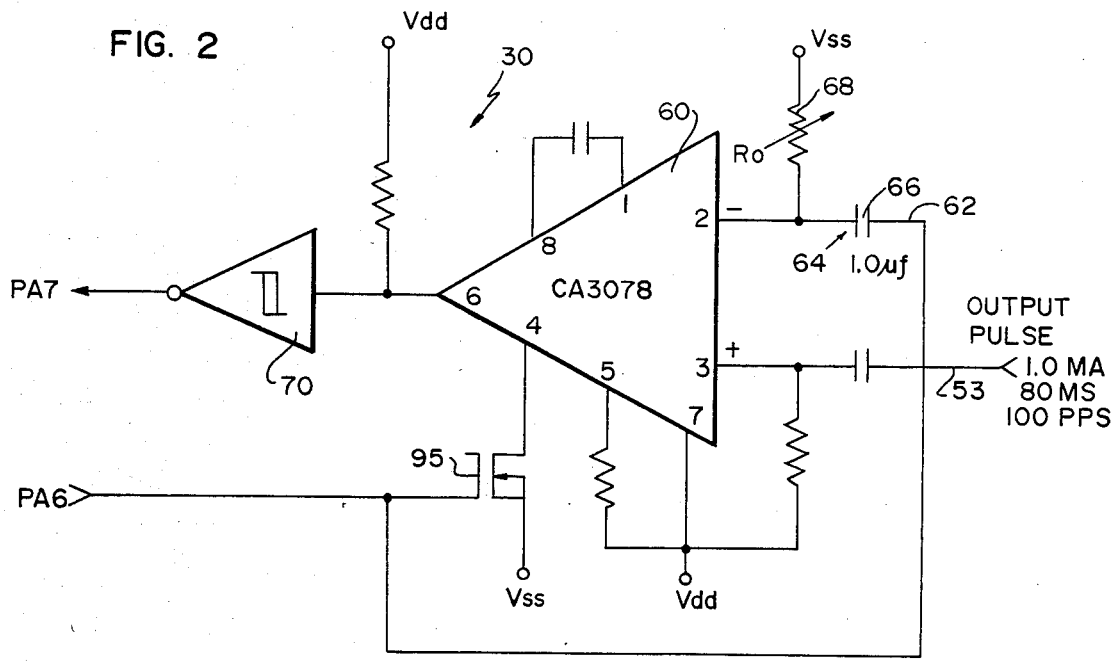
FIG. 2 is a schematic circuit diagram of the electrical circuitry of the apparatus for measuring impedance of the present invention.

As best shown in FIG. 2, the impedance determining apparatus 30 includes an operational amplifier 60 connected as a comparator. This operational amplifier 60 is typically a CA3078 model operational amplifier.

The current pulses that are supplied to the cathode electrode 12 are supplied at a frequency of typically 100 pulses per second and each pulse typically has a duration of 80 microseconds.

Typically, the pulses have an amplitude of 1 milliamp.

In any event, pulses are supplied to an input pin 3 of the comparator 60. At the same time, a voltage from the microprocessor 26 on line PA6 is supplied to line 62 connected to an RC circuit 64 having a capacitor 66 and an adjustable resistor 68. The output of the RC circuit 64 is connected to pin 2 of the comparator 60.

An output pin 6 of the comparator 60 is coupled to an input of a Schmitt trigger circuit 70 which has an output connected to the line PA7 leading to the microprocessor 26.

In utilizing the apparatus 30 for determining and monitoring cathode lead 14 impedance, the microprocessor 26 will periodically initiate a lead impedance measurement over a sampling period of, for example, approximately 400 milliseconds. When this sampling period is initiated, a voltage, such as 3.67 volts, is supplied to the RC circuit 64. The values of the resistor 68 and capacitor 66 in the RC circuit 64 are such that the RC circuit 64 has a predetermined time constant, e.g., a time constant of 0.457. This provides a building up or a ramp voltage on pin 2 of the comparator 60 while pulses are being supplied to pin 3 of the comparator 60.

A typical current output pulse 80 is shown in FIG. 3A. An output pulse generated by a pulse 80, so long as the amplitude of the voltage pulse needed to generate the pulse 80 exceeds the ramp reference voltage 82 (FIGS. 4 and 5), is shown in FIG. 3B and identified by reference numeral 84. Each pulse 84 is passed through the Schmitt trigger circuit 70 and a buffered output pulse 86 is shown in FIG. 3C.

Referring to FIG. 4, there is shown a timing diagram of the beginning of a sampling period for a typical cathode lead impedance of 650 ohms. As shown, the ramp voltage 82 starts from zero and decreases (increasing absolute magnitude of the ramp voltage) toward the lower value of −3.67 volts.

Also, at the same time that this ramp reference voltage 82 is supplied to pin 2 of the comparator 60, voltage pulses necessary to produce the constant current pulses being generated is supplied to pin 3 of the comparator 60 as indicated by pulses 88. When the magnitude of the ramp reference voltage 82 exceeds the magnitude of the pulses 88, the comparator 60 stops generating output pulses. The buffered output pulses 86 are shown at the bottom of the diagram in FIG. 4. These pulses 86 are supplied to the microprocessor 26 via line PA7 and the microprocessor 26 counts those pulses 88 generated from time 0 to time $T_1$ and from that count determines the impedance.

It will be understood that the ramp voltage 82 can be positive or negative so long as the decaying voltage increases in absolute magnitude from the beginning of the sampling period.

The theory of operation of the impedance measuring apparatus 30 is based upon (a) $V_{dd}$ being greater than $V_{ss}$, e.g., $V_{dd}=0$ and $V_{ss}=-3.67$ or $V_{dd}=+3.67$ V and $V_{ss}=0$, (b) the assumption of constant current throughout the measurement range (100–2000 Ω) and (c) a time to voltage conversion.

At the beginning of a sampling period, the microprocessor 26 by itself or in response to telemetered commands will switch the voltage level on line PA6 from $V_{ss}$ to $V_{dd}$. This will energize the operational amplifier 60 through an FET 95. Also, the step change in voltage is differentiated at the negative input on pin 3 by the RC circuit 64. The voltage at the negative input (pin 3) can then be calculated by the following equation:

$$V_0 = V_{max}(1 - e^{-t/\tau})$$

Where: $V_{max}$ is the supply voltage, $\tau = (1.0 \; \mu f)Ro$
$\tau$ = the time constant which is set equal to 0.457.

With a positive input, pin 2 of operational amplifier 60 receives 1.0 mA pulses, and a constant current output yields:

$$R_{load} = \frac{V_0}{1.0 \text{ mA}} = \frac{V_{max}(1 - e^{-t/.457})}{1.0 \text{ mA}}$$

With $V_{max}=3.67$ the only variable left to be determined is time (t). Time (t) is determined from the count of pulses outputted from the operational amplifier/comparator 60.

Each time there is an output pulse 86 on the buffered output line PA7, a register in the microprocessor is incremented. Then, when the decaying voltage at the referenced voltage input (pin 2) crosses or exceeds the magnitude of the voltage pulses 88 at pin 3, the microprocessor 26 will stop incrementing and remove power from the comparator 60. It should be noted that the slew rate of the operational amplifier/comparator 60 is set slow enough for the output of the comparator 60 to extend beyond the pulse 84.

Now time t can be determined. In this respect, with a rate of 100 pps, the time period per count or period is 9.67 ms.

Then:

$$t = 9.767 \times 10^{-3} \times C$$

Where C=number of counts and the output load impedance can be approximated as follows:

$$R_{load} = \frac{3.67}{1.0} \times 10^{-3}(1 - e^{-0.214C})$$

The count information is stored in the RAM of the microprocessor 26 and can be retrieved by telemetry and used by a programmer to calculate load impedance.

As shown in FIG. 5, when there is a higher cathode lead 14 impedance such as 1,000 ohms, the magnitude of the voltage pulses required to maintain the constant current pulses 80 is larger as shown by the pulses 90. As a result, it will take a longer time for the ramp voltage 82 to decrease to the magnitude of the larger-in-amplitude voltage pulses 90 as shown. This results in a larger number of buffered output pulses 86 being generated from the output of the comparator 60 and the microprocessor 26 will count this larger number of pulses and know that there is a greater lead impedance.

This change in lead impedance can be telemetered by the telemetry circuit 40 to exterior analyzing circuitry (not shown) which can then indicate to a physician that the lead impedance has increased and appropriate steps can be taken to find out if there is an open circuit or if there is a buildup of scar tissue around the cathode electrode 12.

While the lead impedance measuring and determining apparatus 30 has been described with particular reference to its use in the neural stimulating system 10, it is to be understood that such impedance measuring apparatus 30 can be utilized in other environments.

Also, it will be apparent from the foregoing description that the method and apparatus for measuring impedance have a number of advantages, some of which have been described above and others of which are inherent in the invention. Also, modifications can be made to the neural stimulating system 10 and the lead impedance measuring apparatus 30 therein without departing from the teachings of the present invention. Accordingly, the scope of the invention is only to be limited as necessitated by the accompanying claims.

I claim:

1. In a neural stimulating apparatus of the type comprising a cathode adapted to be juxtaposed to the spinal cord in a body, in anode adapted to be placed in contact with the body, means for generating constant current output pulses which are supplied to the cathode, a cathode lead coupled between the pulse generating means and the cathode for carrying the pulses to the cathode and means for controlling (a) the generation of pulses and (b) the supplying of pulses to the cathode, the improvement comprising means coupled to the cathode lead for measuring changes in the cathode impedance at the connection of said pulse generating means to the cathode lead, said means for measuring changes in the cathode impedance comprising means for comparing the voltage pulses at which the constant current pulses are being supplied to the load with an increasing reference voltage, means for counting the number of voltage pulses that are greater in magnitude than the increasing reference voltage over a sampling period, and means for correlating said count of pulses over the sampling period with the impedance of the load presented by the lead and connections to tissue required to generate that number of constant current pulses at the voltage required for same.

2. The apparatus of claim 1 wherein said comparing means comprise a comparator having one input coupled to said increasing voltage, another input coupled to said cathode lead and an output coupled to said counting means.

3. The apparatus of claim 2 including means for supplying a reference voltage to said one input of said comparator at the beginning of a sampling period and a capacitor-resistor circuit connected to said one input whereby the reference voltage at said one input will increase slowly until said capacitor is charged.

4. The apparatus of claim 2 including a Schmitt trigger circuit coupled to the output of said comparator.

5. The apparatus according to claim 1 wherein said control means comprise a microprocessor including a timer and a ROM and having an input port coupled to the output of said comparing means.

6. The apparatus according to claim 5 including a power amplifier, a digital/analog converter having an input coupled to output ports of said microprocessor and an output coupled to said power amplifier, said power amplifier having an output connected to said cathode lead and to one input of said comparing means, and said microprocessor having an output port coupled to another input of said comparing means for supplying said reference voltage to said comparing means.

7. The apparatus of claim 6 wherein said comparing means comprise a comparator having said other input coupled to the source of increasing voltage said resistor-capacitor circuit coupled to said other input and said voltage output port of said microprocessor being coupled to said resistor-capacitor circuit.

8. The apparatus of claim 7 wherein the output of said comparator is coupled through a Schmitt trigger circuit to said input port of said microprocessor.

9. The apparatus of claim 7 wherein said resistor-capacitor circuit has a time constant of 0.457.

10. The apparatus of claim 1 wherein said constant current output pulses have a duration of 80 microseconds.

11. The apparatus of claim 1 wherein said constant current pulses are generated at a rate of approximately 100 pulses per second.

12. The apparatus of claim 1 wherein said sampling period is approximately 400 milliseconds.

13. The apparatus of claim 1 wherein said reference voltage is a negative voltage and increases in absolute magnitude from 0 volts to a value of $-3.67$ volts.

* * * * *